United States Patent [19]

Seubert et al.

[11] Patent Number: 4,952,563

[45] Date of Patent: Aug. 28, 1990

[54] WATERFREE APPLICATION FORM OF LOW MOLECULAR WEIGHT ALKALI HUMINATES

[75] Inventors: Bernhard Seubert, Edingen-Neckarhausen; Helmut Beilharz, Schriesheim; Werner Fickert, Mannheim; Günter Jeromin, Heidelberg; Ulrich Spitaler, Freinsheim, all of Fed. Rep. of Germany

[73] Assignee: Rutgerswerke AG, Fed. Rep. of Germany

[21] Appl. No.: 162,803

[22] Filed: Mar. 1, 1988

[30] Foreign Application Priority Data

Mar. 21, 1987 [DE] Fed. Rep. of Germany ....... 3709353

[51] Int. Cl.$^5$ ...................... A61K 31/70; C07H 15/00
[52] U.S. Cl. ..................................... 514/33; 514/770; 536/17.1; 536/17.3
[58] Field of Search ................ 514/33, 770; 536/17.1, 536/17.3

[56] References Cited

PUBLICATIONS

Kingzette's–Chemical Encyclopedia (London) 9th ed, 1969, p. 483.
Chemical Abstracts 107:235411b (Adhikari et al.) 1987.
Chemical Abstracts 105:171313v (Adhikari et al.) 1986.
Chemical Abstracts 103:98707d (Zeng et al.) 1985.

*Primary Examiner*—Leonard Schenkman
*Attorney, Agent, or Firm*—Bierman and Muserlian

[57] ABSTRACT

The invention relates to a new application form of low molecular weight alkali metal huminates wherein the waterfree low molecular weight alkali metal huminate is bound to an inorganic, hydrogen bridge forming, carrier material such as titanium dioxide, aluminum oxide, highly dispersed silicium dioxide, or clay.

4 Claims, No Drawings

WATERFREE APPLICATION FORM OF LOW MOLECULAR WEIGHT ALKALI HUMINATES

STATE OF THE ART

The invention relates to a new application form of low molecular weight alkali metal huminates. It has recently become known that these low molecular weight alkali metal huminates can be employed as therapeutic agents, in particular, in the area of wound healing (German applications No. P 3,707,909.3 and P 3,707,910.7). In connection thereto, these huminates are most frequently used as a 1 to 5 percent aqueous solution. Such solutions can be concentrated further; however, no waterfree low molecular weight alkali metal huminate could be prepared as the huminate is irreversibly destroyed during the process. However, in other forms such as waterfree salves, adhesive pastes, or sprays, the active agent is needed in a waterfree state.

Ziechmann, "Huminstoffe", publ. Chemie 1980, page 284, discloses that humic matter forms complexes with clay. However, the humic matter in these complexes is catalyzed by the clay material and is further oxidized to higher molecular weight substances. Additionally, the humic matter cannot subsequently be freed from these clay complexes by adding water. Instead, they can be freed only through the action of an alkali solution at an increased temperature with the concomitant change in their structure.

OBJECTS OF THE INVENTION

It is therefore an object of the invention to obtain a waterfree application form of a low molecular weight alkali metal huminate from which the huminate can be readily freed upon contact with water without the efficacy thereof being changed compared to the original aqueous solution.

This and other objects and advantages of the invention will become obvious from the following detailed description.

THE INVENTION

It has been found that low molecular weight alkali metal huminates can have water removed without undergoing any chemical change if they are present in a mixture with hydrogen bridge forming inorganic carrier materials. The complexes originating therein or adducts thereof are stable, pourable products from which, by the addition of water, the low molecular weight alkali metal huminates can be freed in their original structure and original physiological activity.

Carrier materials usable according to the invention include all hydrogen bridge forming inorganic materials such as aluminum oxide, titanium dioxide, highly dispersed silicium dioxide, or clay. Preferable are montmorillonite, or bentonite. Surprisingly, natural and synthetic low molecular weight alkali metal huminates with an average molecular weight of 1,000, and a molecular weight range from 300 to 1,500 form, with the bridge materials, complexes or adducts which are, on the one hand, stable and not subject to autoxidation or other humification processes and which are, on the other hand, easily split by the hydration forces of water at room temperature.

It is further surprising that the labile huminate molecules, when fixed to the hydrogen bridge forming inorganic carrier material, can have water removed without further dehydration reactions and structural changes, even when heated to temperatures of 100° C. Low molecular weight alkali metal huminates are hygroscopic substances if they contain less than 5 percent water. It is a further surprising advantage of the invention that these properties are lost if the alkali metal huminate is bound to the inorganic carrier material.

For preparing the waterfree application forms, 1 to 5 percent aqueous solution obtained in the preparation of the low molecular weight alkali metal huminate or a concentrated solution, is made into a paste using 0.2 to 5 times the stoichiometric volume of the inorganic carrier material. The resulting mixture is then dried either through vacuum treatment or other known means or through heating to a temperature up to 110° C. It is advisable in connection with this treatment, to stir the substance during the drying process to avoid clumping. The subsequently obtained pourable brown powder is storable without further protective means, can be incorporated into powders or sprays alone or with auxiliary matter, and can be readily mixed with a waterfree salve foundation such as vaseline or viscous paraffin to form a waterfree paste.

Various modifications of the product and process of the invention may be made without departing from the spirit or scope thereof and it should be understood that the invention is intended to be limited only as defined in the appended claims.

What we claim is:

1. A waterfree form of an alkali metal huminate with an average molecular weight of about 1,000 wherein the waterfree alkali huminates are bound to an inorganic hydrogen bridge forming carrier material selected from the group consisting of titanium dioxide, aluminum oxide, highly dispersed silicium dioxide and clay with a volume ratio of huminate to carrier material of 1:0.2 to 1:5.0.

2. The waterfree form of claim 1 wherein the inorganic carrier material is montmorillonite or bentonite.

3. A method for preparing the waterfree form of claim 1 comprising mixing an aqueous solution of alkali metal huminate with an average molecular weight of about 1,000 with an inorganic carrier material selected from the group consisting of the waterfree form of claim 1 wherein the carrier material is selected from the group consisting of titanium dioxide, aluminum oxide, highly dispersed silicium dioxide and clay in a volume ratio of huminate to carrier material of 1:0.2 to 1:5.0 and drying the obtained mixture at temperatures up to 110° C.

4. A wound healing composition comprising a waterfree salve, powder or adhesive paste containing an effective amount of the product of claim 1.

* * * * *